United States Patent [19]

Maisano et al.

[11] Patent Number: 6,022,524

[45] Date of Patent: Feb. 8, 2000

[54] PROCESS FOR THE CONJUGATION OF CHELANTS WITH MOLECULES CONTAINING AMINO GROUPS

[75] Inventors: Federico Maisano; Luigia Gozzini, both of Milan, Italy

[73] Assignee: DIBRA S.p.A., Italy

[21] Appl. No.: 09/061,021

[22] Filed: Apr. 16, 1998

[30] Foreign Application Priority Data

Apr. 18, 1997 [IT] Italy ................... MI97A0929

[51] Int. Cl.[7] .......................... A61K 51/08; A61K 38/00; A61B 5/055; C07F 5/00; C07C 315/00

[52] U.S. Cl. .................. 424/1.69; 424/9.36; 424/9.361; 424/9.364; 534/10; 534/14; 530/300; 530/303; 530/401; 530/362; 562/566; 540/465

[58] Field of Search .................. 424/1.65, 1.69, 424/1.49, 9.36, 9.364, 9.361, DIG. 16, 1.45; 540/465, 474; 560/54, 76, 127, 190, 480; 562/565, 590, 566; 514/574; 534/10–16; 530/300, 303, 401, 362

[56] References Cited

U.S. PATENT DOCUMENTS 5,338,532  8/1994  Tomalia et al. .................. 424/1.49

OTHER PUBLICATIONS

Paxton, et al. "Improved Method for the Synthesis of DTPA Conjugates," Cancer Research, 45, pp. 5694–5699, Nov. 1985.

*Primary Examiner*—Jose' G. Dees
*Assistant Examiner*—Michael G. Hartley
*Attorney, Agent, or Firm*—Nixon & Vanderhye

[57] ABSTRACT

A process for the preparation of macromolecular chelants characterized by a high content in chelant groups per macromolecule.

11 Claims, No Drawings

PROCESS FOR THE CONJUGATION OF CHELANTS WITH MOLECULES CONTAINING AMINO GROUPS

The present invention relates to a method for the preparation of macromolecular chelants characterized by a high content in chelant groups per macromolecule. After complexation with suitable metal ions, said compounds can be used, as such or in combination or formulation with other components, in diagnostic imaging as general or specific contrast agents for a certain tissue, organ or body district.

In diagnostic imaging with nuclear magnetic resonance (MRI), high amounts of paramagnetic metal ions, such as gadolinium, have to be administered in order to reach and keep for some time a high signal in specific body districts. The high toxicity of these metal ions can be reduced to a great extent by complexation with suitable chelants, such as diethylenetriaminopentaacetic acid (DTPA); moreover, a sufficiently long-lasting signal is usually obtained by binding these complexes to a macromolecule, for example a protein such as serum albumin (Ogan M. D. et al., Invest. Radiol. 22,665–671, 1987). The preparation of these conjugates of DTPA with macromolecules is usually carried out by reacting DTPA dianhydride, a commercially available product, with suitable reactive functional groups of the selected macromolecule, such as the amino groups. This method, however, suffers from a number of drawbacks, in that the reaction is not specific and both inter- and intra-molecular bridges (cross-linking) are introduced on the macromolecule, due to the double functionality of the used reactive (Maisano F. et al., Bioconj. Chem. 3, 212–217, 1992). The higher the molar ratio of DTPA dianhydride to macromolecule reactive groups in the conjugation reaction, the more serious said drawbacks. On the other hand, high molar ratios are essential to obtain appreciable conjugation levels, due to the instability of the anhydride in aqueous medium.

In order to overcome these problems, methods have been proposed requiring a complex, expensive synthesis of chelants monofunctionalized with groups specifically reacting with the amino groups of the macromolecule, such as the isothiocyanate group (see for ex. Brechbiel M. W. et al. Inorg. Chem. 25, 2772–2781, 1986; Westerberg D. A. et al., J. Med. Chem. 32, 236–243, 1989). Alternatively, methods envisaging a pre-activation of the chelant in the form of N-succinimido ester and the subsequent reaction with the amino groups of the macromolecule have also been described (Buckley R. G. and Searle F. FEBS Lett. 166, 202–204, 1984; Paxton R. J. et al. Cancer Res. 45, 5694–5699, 1985). The latter alternative, although apparently promising, has not have an adequate development for introducing a high number of chelant groups, as it is necessary in MRI imaging. Said method was in fact described and developed only to conjugate chelates of radioactive metals with antibodies, in view of their use in scintigraphy. This diagnostic technique requires of course extremely low dosages and therefore a great number of chelants conjugated with the macromolecule are of no interest to the researcher of the field.

The present invention overcomes these problems, in that it allows to bind a high number of chelants to the macromolecule, avoiding at the same time non specific reactions, as well as any inter- or intra- molecular cross-linkings. The method object of the present invention is based first on a preactivation of the chelant to conjugate with the macromolecule, transforming it into a suitable reactive derivative, such as, preferably, a N-succinimido ester [analogously to what already known from the prior art]. Nevertheless, contrary to the already described methods, this method provides exceedingly high conjugation levels, thanks to the subsequent original multistep procedure which, besides obviating all the known synthetic difficulties, also makes the application on the industrial scale possible. The preactivation of the chelant as N-succinimido ester is not, in fact, capable alone of giving the necessarily high conjugation levels, even in the presence of a strong molar excess of reactive ester to available amino groups, mainly for two reasons:

a) the chelant groups conjugated with the macromolecule exert an electrostatic repulsion towards other chelant molecules, thereby decreasing the reactivity of the still free, spatially close amino groups; moreover b) in the conjugation conditions, the reactive ester undergoes a simultaneous hydrolysis reaction which inhibits its reactivity.

As a consequence, even strong excesses of reactive ester, longer reaction times or more drastic reaction conditions provide no improvements in the total yield of the process. On the contrary, the formation of inner salt bridges between free amino groups and molecules of already conjugated chelant, worsens the situation.

It has now unexpectedly been found that when, after a first conjugation step effected with a reactive ester molar excess and in mild reaction conditions (not high temperature and reaction time), the introduced chelating groups are complexed with suitable metal cations, including radioisotopic metals, their inhibiting action on the reactivity of spatially close amino groups markedly decreases. At this point, a second conjugation reaction allows to bind other chelant molecules also to those amino groups which could not react before.

It is therefore object of the present invention a process for the preparation of conjugates between polyaminopolycarboxylic chelants and molecules containing amino groups, substantially comprising the following steps:

formation of a reactive ester, such as, preferably, a N-succinimido ester of the desired chelant, by condensation of the chelant with N-hydroxysuccinimide (NHS), in the presence of a suitable dehydrating agent, such as carbodiimide, reaction of this ester with the molecule containing the amino groups, being the ester in molar excess to the amino groups of said molecule, purification of the resulting conjugate from the excess chelant and subsequent complexation of the conjugate with a metal ion, second conjugation reaction between the complexed conjugate and the chelant N-succinimido ester, being the ester in molar excess to the residual amino groups, purification of the final conjugate from the excess chelant and subsequent second complexation of the residual chelants introduced with a metal ion.

A particularly preferred embodiment of the process according to the present invention comprises:

preparation of the N-succinimido ester of the polyaminopolycarboxylic chelant, preferably DTPA or DOTA, by reaction with NHS, in the presence of dicyclohexylcarbodiimide in an aprotic solvent selected from acetonitrile, dimethylsulfoxide, dimethylformamide and optionally in the presence of an organic base, subsequent concentration of said ester by evaporation under vacuum of most solvent, i.e. about 90%;

gradual addition of the ester concentrated solution to an aqueous solution of the amino group containing-molecule, keeping pH between 6 and 10 by the simultaneous addition of a base, preferably NaOH; when the ester amount, calculated on the basis of the starting chelant, is in a 5–250, preferably 6–100, molar excess, to the amino groups present in the molecule and the reaction time ranges from 1 to 48 hours from the end of the additions of the ester, at a temperature from 15 to 40° C., purification of the resulting conjugate from by-products, impurities and excess reagents by membrane (dialysis or ultrafiltration), or chromatographic (ion exchange or steric exclusion chromatographies) processes, or by a combination thereof, complexation of the conjugate with a metal ion or a salt thereof and optional subsequent removal of the excess metal, a second conjugation reaction between the still free amino groups of the complexed conjugate with a molar excess of the N-succinimido ester chelant, in the conditions described above, second purification of the conjugate from the reaction by-products by means of membrane or chromatographic processes, complexation of the final conjugate with a metal ion and optional subsequent purification treatments to remove the excess metal and/or to improve the homogeneity of the compound.

Polyamine macromolecules susceptible of conjugation according to the above described method comprise, for example, bovine serum albumin, insulin, cytochrome C, myoglobin, dendrimers, polylysines and the like. Among the most suitable metal ions, $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$ can be cited, whereas the radioisotopic ions can be $^{51}Cr$, $^{67}Ga$, $^{68}Ga$, $^{111}In$, $^{99m}Tc$, $^{140}La$, $^{175}Yb$, $^{153}Sm$, $^{166}Ho$, 90y, $^{149}Pm$, $^{177}Lu$, $^{47}Sc$, $^{142}Pr$, $^{159}Gd$, $^{212}Bi$.

The method of the invention provides chelate/macromolecule conjugation percentages exceedingly higher than those of the teachings of the prior art. It is moreover possible to obtain metal complex conjugates characterized by a chelant/amino groups total substitution degree of at least 50% and, depending on the macromolecule used, even higher than 60/70%. Furthermore, non specific and cross-linking reactions are prevented. The purification of the final mixture from the undesired impurities (in this case only the excess chelant and N-hydroxysuccinimide) is therefore easier, as exemplified in the following Experimental section.

EXAMPLE 1

Preparation of Gd-DTPA—Bovine Serum Albumin Conjugate

A solution of 40 g DTPA (0.102 mol) in 1.2 l of dry dimethylsulfoxide (DMSO) is prepared by heating and stirring, then it is cooled at room temperature and added with a solution of 11.73 g NHS (0.102 mol) in 300 ml DMSO, then, drop by drop, with a solution of 19.6 g of N,N'-dicyclohexylcarbodiimide (0.097 mol) in 400 ml DMSO. The mixture is stirred for 16 hours, then filtered and the filtrate is concentrated by evaporation at 50° C. and 5 Pa to a thick oil of an about 160 ml volume.

This oil is added in portions to a solution of 1 g of bovine serum albumin (BSA; 15 µmol, 60 amino groups/molecule) in 1 l of 0.1 M borate buffer pH 8, 0.1 M NaCl, keeping pH at 8 by the simultaneous addition of 2 N NaOH. At the end of the additions, the mixture is stirred for 16 hours, then filtered and purified from by-products and excess reagents by chromatographic desalting on a Sephadex G-25 column (8.9×50 cm). The protein solution is then concentrated by ultrafiltration (S1Y30 cartridge, Amicon) to a volume of 100 ml. This solution is added with 10 ml of a 0.6 M solution of the complex of gadolinium with nitrilotriacetic acid at pH 6 and equilibrated for 1 hour, after that it is diluted to 2 l with borate buffer pH 8 and concentrated again to 100 ml by ultrafiltration.

The resulting compound contains about 25 Gd-DTPA residues per albumin molecule. To further increase this ratio, the solution of the complexed conjugate is treated again with the N-succinimido ester as described above, and subjected again to the described purification and complexation procedures. After the complexation, the compound is finally purified by steric exclusion chromatography on a Sephacryl S-200 HR column (65 cm×9 cm diam.) eluting with 0.15 M NaCl. This chromatography also purifies the compound from the dimer and aggregates percentages originally present in the commercial BSA, thereby providing a conjugate with 45 Gd-DTPA residues per protein molecule (75% of the 60 amino groups of BSA), which is chromatographically homogeneous and free from cross-linking and from free Gd-DTPA.

The determination of the substitution degree was effected referring the gadolinium concentration to that of the protein, determined by X-ray fluorescence (XRF) and spectrophotometric absorption at 280 nm ($e_{280\ nm}$=0.66 $L.g^{-1}.cm^{-1}$), respectively.

TABLE 1

Characteristics of the compounds described in example 1.

| Compound | Gd mol/ mol BSA | Substitution degree | % aggregates |
| --- | --- | --- | --- |
| Commercial BSA | — | 0 | 20–25% |
| Gd-DTPA-BSA (1 conjug.) | 25 | 42% | 20–25% |
| Gd-DTPA-BSA (2 conjug. + purif.) | 45 | 75% | 0 |

EXAMPLE 2

Preparation of Conjugates of Other Proteins With Gd-DTPA

According to the same procedure, Gd-DTPA was conjugated with porcine insulin, equine cytochrome C, equine myoglobin, to obtain conjugates containing 3, 13 and 12 Gd-DTPA residues/protein respectively, corresponding to 100%, 68% and 60% amino groups substitution (see Table 2).

TABLE 2

Characteristics of the compounds described in example 2

| Compound | Starting amino groups | Gd mol/ mol BSA | Substitution degree |
| --- | --- | --- | --- |
| Gd-DTPA-insulin | 3 | 3 | 100% |
| Gd-DTPA-cytochrome C | 19 | 13 | 68% |
| Gd-DTPA-myoglobin | 20 | 12 | 60% |

We claim:

1. A process for conjugating polyaminopolycarboxylic chelants with amino groups of macromolecules, which process comprises the steps of:

(a) activating polyamino polycarboxylic chelants by forming a reactive ester of the chelant;

(b) conjugating the reactive esters formed in step (a) with amino groups of the macromolecules to functionalize the macromolecules;

(c) removing any unreacted chelant and forming a metal complex of the conjugate from step (b);

(d) reacting the metal complex with the reactive chelants of step (a); and (e) removing any unreacted chelant and again complexing with metal ions.

2. The process according to claim 1, in which step (a) is carried out by condensing, optionally in the presence of an organic base, the polyaminopolycarboxylic chelant with N-hydroxysuccinimide in the presence of a dehydrating agent in an aprotic solvent.

3. The process according to claim 1 in which step (b) is carried out in an aqueous medium at pH from 6 to 10 and in the presence of a molar excess of activated chelant from step (a) to the number of amino groups of the macromolecules.

4. The process according to claim 1 which step (c) is carried out first removing impurities, by-products and excess reagents by membrane and/or chromatographic processes, and then reacting the resulting conjugate with a metal ion or a salt thereof.

5. The process according to claim 1, in which step (d) is carried out by reacting free amino groups of a complexed conjugate with a reactive chelant present in molar excess.

6. The process according to claim 2, in which the dehydrating agent is dicyclohexylcarbodiimide and the aprotic solvent is selected from the group consisting of acetonitrile, dimethylsulfoxide and dimethyl formamide.

7. The process according to claim 3, in which the reactive ester of the chelant is present in a 5 to 250 molar excess to the amino groups, pH is kept between 6 and 10 by addition of NaOH, the reaction time ranges from 1 hour to 48 hours from the end of the addition of the reactive ester of the chelant, and the reaction temperature is kept from 15° to 40° C.

8. The process according to claim 1, in which impurities, by-products and excess reagents are removed by dialysis, ultrafiltration, ion exchange, steric exclusion chromatographies, or combinations thereof.

9. The process according to claim 4, in which the polyaminopolycarboxylic chelant is selected from the group consisting of DTPA and DOTA.

10. The process according to claim 1, in which the macromolecule is a polyamine selected from the group consisting of bovine serum albumin insulin, cytochrome C, myoglobin, dendrimers and polylysines.

11. The process according to claim 1, in which the metal in the metal complex is selected from $Cr^{(3+)}$, $Gd^{(3+)}$, $Eu^{(3+)}$, $Dy^{(3+)}$, $La^{(3+)}$, $Yb^{(3+)}$ or $Mn^{(2+)}$ or from the ions of the following radioisotopes: $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$, and $^{212}Bi$.

* * * * *